United States Patent [19]

Bennett

[11] Patent Number: Plant 6,453

[45] Date of Patent: Dec. 13, 1988

[54] MINIATURE ROSE PLANT 'MY SUNSHINE'

[76] Inventor: Cecilia L. D. Bennett, 489 Minot Ave., Chula Vista, Calif. 92010

[21] Appl. No.: 10,718

[22] Filed: Feb. 4, 1987

[51] Int. Cl.[4] ..... A01H 5/00

[52] U.S. Cl. ..... Plt./8

[58] Field of Search ..... Plt. 8

*Primary Examiner*—James R. Feyrer

[57] ABSTRACT

The subject of the present disclosure is a new and distinct variety of miniature rose plant, named 'My Sunshine', which is characterized by its golden-yellow blooms, ranging from Buttercup Yellow to Indian Yellow, with exactly one row of five petals and usually borne one to a stem or in sprays of 3 to 5 or more blooms. The bush is vigorous and well-branched, producing moderate to heavy quantities of bloom.

The present invention relates to a new and distinct variety of a hardy, dwarf, bush plant of the miniature class; the variety being primarily characterized as medium yellow.

The variety is further characterized by:

Long stemmed blooms of five petals only, borne usually one to a stem but on occasion in sprays of 3 to 5 or more. The blooms are held very erect and well above the foliage.

It has a moderate amount of fragrance.

The plant ranges in height from 15 to 24 inches (40 to 60 cm). The canes are sturdy and erect with moderate to heavy branching and medium foliage covering. The plant is a moderate to heavy bloomer that does well either in the greenhouse or outdoors.

The plant has good growth habits, well-shaped and attractive, bearing numerous leaflets of average size.

The seed parent was Sunsprite (U.S. Plant Pat. No. 3,509), and the pollen parent was Fool's Gold (miniature rose plant, orange blend; Jack Christensen; introduced by Armstrong Nursery, 1984. It differs from its seed parent in the following ways. It is a miniature rose with only one row of five petals, and Sunsprite is a floribunda rose with a larger bloom and hybrid tea form with 25 to 30 petals. It differs from its pollen parent in the following ways. It is a five-petaled bloom of medium yellow, and Fool's Gold has hybrid tea-type bloom of orange blend.

The descriptive matter which follows pertains to roses grown and color values observed in plants and newly opened blooms in the months of March through August 1986. The plants were grown outdoors in Chula Vista, Calif., and are believed to be accurate standards for this cultivar in similar conditions of soil and climate elsewhere.

The color photograph illustrates the variety.

1 Drawing Sheet

Referring now specifically to the new and distinct variety of miniature rose plant named 'My Sunshine', the following is a detailed description thereof in outline; all major color plate identifications being by reference to The British Colour Council Horticultural Colour Chart, except where common terms of color definition are employed.

Type: Hardy, dwarf, bushy, greenhouse or outdoor, exhibition quality or garden decorative potted plant.

Class: Miniature.

Variety name: My Sunshine.

Flowers borne: Usually one to a stem, but occasionally in sprays of 3 to 5 or more on erect stems with foliage well below the blooms.

Quantity of bloom: Moderate to heavy both outdoors or greenhouse grown.

Bud:

*Peduncle.*—Average length (25 to 30 mm); average diameter and sturdy; ranging from near Scheeles Green (860/3 to 860/2 page 860) to near Lettuce Green (861/3 to 861/1 page 861) with occasional tinting of bronze.

*Hairs.*—Extremely small and numerous with a reddish color; located over the entire surface of the peduncle and sepals, but not present on the calyx tube.

*Calyx.*—Color range same as peduncle.

*Opening.*—Opens well in all weather.

Bloom:

*Size when fully open.*—Average for a miniature variety (35 to 40 mm).

*Petalage.*—Single — Five petals arranged regularly without petaloids.

*Form.*—Urn-shaped bud that opens to a flat five-petaled bloom. No reflexing of the margins is present in the open bloom.

Petals: Fairly thick with good substance; both the upper and under surfaces of all petals have a matte finish.

*Shape.*—All petals are of a very broad obovate form with a slight peak at the apex.

Color: Newly opened flowers from plants grown outdoors (March through August of 1986), Chula Vista, Calif.

*All petals.*—Upper and Under Surfaces — Ranging from near Buttercup Yellow (5/1 to 5 page 5) to near Indian Yellow (6/1 to 6 page 6). After 3 to 5 days open, the color fades, ranging from near Buttercup Yellow (5/3 to 5/2 page 5) to near Indian Yellow (6/3 to 6/1 page 6) with slight blush of near Majolica Yellow (09/1 to 09 page 09) at the apex of the aged bloom.

*General color effect.*—Newly opened flowers — Bright golden yellow. Three days open — Some fading of the yellow with a slight blush of golden-orange at the apex of each petal. Five to seven days — Petals fading to very pale yellow with deepening of the blush at the apex of the petals.

*Flower longevity.*—(March through August of 1986) Plant in pot 1 to 2 days from bud to fully opened bloom. Holding at fully opened with gradual fading of the yellow tones and an increase in the blush on the apex for 3 to 5 days or longer. Cut blooms at living room temperature 3 to 5 days or longer.

Reproductive organs:

*Stamens.*—A generous amount arranged uniformly around the pistil.

*Filaments.*—Varying in length with shorter filaments more proximal to the pistil; golden yellow including the anthers.

*Pollen.*—Abundant.

*Pistil.*—Short, abundant and compact; pale yellow overall.

*Ovaries.*—All encased in calyx.

*Hips.*—Some.

*Seeds.*—3 to 5 or more in each hip.

*Sepals.*—Permanent; spear-shaped; open as the bloom opens; recurving against the peduncle, when the bloom is fully opened.

Foliage:

*Leaves.*—Five to seven leaflets on the average; medium size for a miniature rose plant.

*Leaflets.*—Broad ovate-shaped.

*Margins.*—Very serrated with tinting of bronze, especially noticeable on the newer foliage.

*Color.*—Ranging from near Scheeles Green (860/3 to 860 page 860) to near Lettuce Green (861/3 to 861/1 page 861) with occasional bronzing of the margins, especially on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to medium; average width; tapering auricles angled outward at about 45 degrees.

Growth:

*Habit.*—Dwarf, bushy; average height for a miniature rose plant.

*Growth.*—Vigorous and well-branched.

*Canes.*—Medium diameter; sturdy; held erect.

*Main stems.—Color*—Ranging from near Scheeles Green (860/3 to 860 page 860) to near Lettuce Green (861/3 to 861/1 page 861).

*Thorns.*—Averaging 10 to 15 per 10 cm on the main stems and fewer on the branches. Pale yellow in color with an occasional tinting of bronze.

*Branches.—Color*—Same as main stems.

The miniature rose plant and its flowers as herein described may vary in slight detail due to climate, soil and cultural conditions under which the variety may be grown; the present description being of the variety as grown in Chula Vista, Calif.

I have found this variety to be easily asexually reproduced from cuttings, with flowers borne usually one to a stem but occasionally in sprays of 3 to 5 or more.

The following is claimed:

1. A new and distinct variety of miniature rose plant named, 'My Sunshine' of hardy, dwarf, vigorous growth, well-branched and attractive in appearance, substantially as illustrated and described, characterized by its five-petaled blooms of bright yellow, ranging from near Buttercup Yellow to near Indian Yellow.

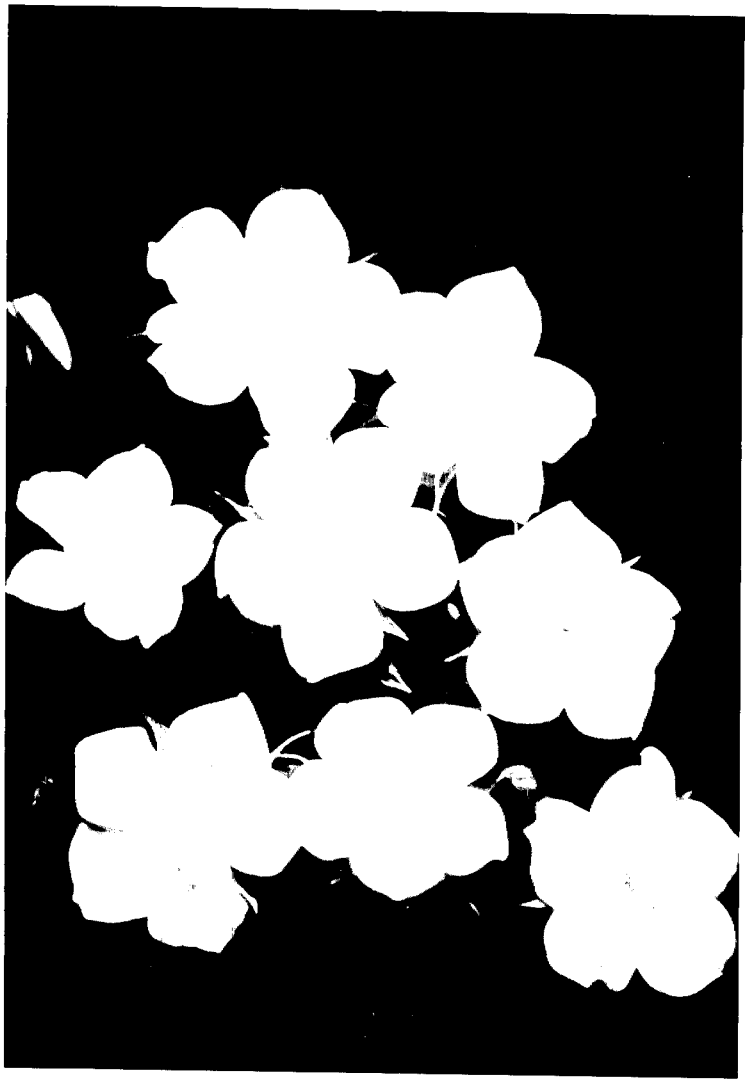

* * * * *